US008546605B2

(12) United States Patent
Kloetzer et al.

(10) Patent No.: US 8,546,605 B2
(45) Date of Patent: Oct. 1, 2013

(54) PROCESS FOR THE PREPARATION OF ISOCYANATES

(75) Inventors: Matthias Kloetzer, Kroppen (DE); Eckhard Stroefer, Mannheim (DE); Volker Krase, Lauchhammer (DE); Andreas Schmidt, Schwarzheide (DE); Peter Scherbel, Schwarzheide (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 858 days.

(21) Appl. No.: 12/065,680

(22) PCT Filed: Sep. 5, 2006

(86) PCT No.: PCT/EP2006/066028
§ 371 (c)(1),
(2), (4) Date: Mar. 4, 2008

(87) PCT Pub. No.: WO2007/031444
PCT Pub. Date: Mar. 22, 2007

(65) Prior Publication Data
US 2008/0249332 A1 Oct. 9, 2008

(30) Foreign Application Priority Data
Sep. 13, 2005 (DE) .......................... 10 2005 043 799

(51) Int. Cl.
*C07C 291/00* (2006.01)
(52) U.S. Cl.
USPC ............ 560/344; 560/330; 560/336; 560/338
(58) Field of Classification Search
None
See application file for complete search history.

(56) References Cited

U.S. PATENT DOCUMENTS

| 4,290,970 | A | | 9/1981 | Merger et al. | |
|---|---|---|---|---|---|
| 4,388,238 | A | | 6/1983 | Heitkaemper et al. | |
| 4,497,963 | A | | 2/1985 | Merger et al. | |
| 4,596,678 | A | | 6/1986 | Merger et al. | |
| 4,847,408 | A | * | 7/1989 | Frosch et al. | 560/347 |
| 5,386,053 | A | * | 1/1995 | Otterbach et al. | 560/344 |
| 5,931,579 | A | | 8/1999 | Gallus et al. | |
| 2006/0123842 | A1 | | 6/2006 | Sohn et al. | |

FOREIGN PATENT DOCUMENTS

| CA | 1117969 | 2/1982 |
|---|---|---|
| EP | 0 018 588 | 11/1980 |
| EP | 0 027 952 | 5/1981 |
| EP | 0 028 338 | 5/1981 |
| EP | 0 126 299 | 11/1984 |
| EP | 0 566 925 A2 | 10/1993 |
| EP | 0 830 894 A1 | 3/1998 |
| WO | WO 2004/056756 A1 | 7/2004 |

OTHER PUBLICATIONS

E.B.Nauman, Chemical reactor design, optimization and scaleup, 2002.*
U.S. Appl. No. 12/446,460, filed Apr. 21, 2009, Boehling, et al.
U.S. Appl. No. 13/125,895, filed Apr. 25, 2011, Geissler, et al.

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

The invention provides a multistage process for continuously preparing organic, distillable polyisocyanates, preferably diisocyanates, more preferably aliphatic or cycloaliphatic diisocyanates, by reacting the corresponding organic polyamines with carbonic acid derivatives and alcohols to low molecular mass monomeric polyurethanes, and thermally cleaving said polyurethanes, in which at defined reaction stages the polyisocyanates prepared and unusable residues are separated off, and reusable by products and intermediates are recycled to upstream stages.

21 Claims, No Drawings

PROCESS FOR THE PREPARATION OF ISOCYANATES

The invention provides a multistage process for continuously preparing organic, distillable polyisocyanates, preferably diisocyanates, more preferably aliphatic or cycloaliphatic diisocyanates, by reacting the corresponding organic polyamines with carbonic acid derivatives and alcohols to low molecular mass monomeric polyurethanes and thermally cleaving said polyurethanes, in which at defined reaction stages the polyisocyanates prepared and unusable residues are separated off while reusable by products and intermediates are recycled to upstream stages.

The industrial processes for preparing organic polyisocyanates, such as aromatic, aliphatic or cycloaliphatic polyisocyanates, are based on the phosgenation of the corresponding organic polyamines to polycarbamoyl chlorides and the thermal cleavage of said chlorides to the polyisocyanates and hydrogen chloride. Apart from the grave environmental, disposal, and safety problems which accompany the use of phosgene, these processes are burdened with further critical disadvantages. For instance, owing to the relatively high basicity of the starting polyamines, the preparation of aliphatic or cycloaliphatic polyisocyanates is accomplished only with rather moderate space-time yields. A further disadvantage is the formation of unwanted byproducts, which even in traces can lead to severe discoloration of the polyisocyanates. In the case of the preparation of hexamethylene 1,6-diisocyanate (HDI), for example, a number of byproducts are formed, of which the most important, 6-chlorohexyl isocyanate, possesses the further disadvantage that it can be separated from the HDI only with considerable distillative cost and effort.

Particular problems associated with this procedure are the high conversion of chlorine via phosgene and carbamoyl chloride into hydrogen chloride, the toxicity of the phosgene, the corrosiveness of the reaction mixture, the instability of the solvents commonly employed, and the formation of halogenated residues.

Despite the fact that the thermal cleavage of (cyclo)aliphatic and especially aromatic monourethanes and diurethanes into the corresponding isocyanates and alcohol has been known for a long time and can be performed not only in the gas phase at high temperatures but also in the liquid phase at comparatively low temperatures, the process economics are affected adversely and sustainedly by, in particular, the unwanted side reactions, and especially the tendency of the reaction mixtures to form coatings, resinous masses, and blockages in reactors and processing equipment.

In the past decades, therefore, there have been many efforts made to eliminate these process disadvantages by means of a simpler, improved process. For instance, for the preparation of aliphatic and/or cycloaliphatic diurethanes and/or polyurethanes, in accordance with EP 18588 A1 or else as in EP 28338 A2, primary aliphatic and/or cycloaliphatic diamines and/or polyamines have been reacted with O-alkylcarbamidic esters in the presence of alcohols at temperatures from 160 to 300° C., both with and without catalyst. The resultant diurethanes and/or polyurethanes can be converted into the corresponding isocyanates. The ammonia formed in the reaction of the amines can be separated off.

Further publications concern themselves with the partial replacement of urea and/or diamines by carbonyl compounds (e.g., EP 27952 or EP 126299). The phosgene-free process is described at length in, for example, EP 566925 A2.

A disadvantage of the latter process is the relatively long reaction time, reported as up to 50 hours.

It is an object of the present invention to prepare distillable organic polyisocyanates, especially aliphatic and cycloaliphatic diisocyanates, with high selectivity in improved space-time yields, simply and cost-effectively, without the use of expensive and/or safety-jeopardizing starting materials or auxiliaries.

It has proven possible to achieve this object by means of a process for preparing isocyanates by reacting at least one amine with urea and at least one alcohol to the corresponding urethane in at least one mixing means with at least one attached residence-time reactor and subsequently cleaving the resultant urethane into the corresponding isocyanates.

The invention provides a multistage process for continuously preparing organic isocyanates by reacting the corresponding organic amines with urea and at least one alcohol to the corresponding urethanes in at least one mixing means with downstream reactor and thermally cleaving said urethanes, said process comprising the following stages and entailing a) reacting at least one organic amine with urea in the presence or, preferably, in the absence of at least one catalyst and in the absence or, preferably, in the presence of at least one alcohol to the corresponding urethanes in at least one mixing means, b) reacting the mixture obtained from a) in at least one following residence-time reactor or two or more residence-time reactors which from their residence-time distribution resemble a tube reactor, c) separating off the ammonia that is formed, d) from the discharge from c), separating off excess alcohol and other low-boiling secondary components, e) supplying at least some of the urethane from (d) that has been freed from the alcohol and low-boiling components to a distillation, f) cleaving the urethanes in the distillate from (e) and, if appropriate, the fraction from (d) not supplied to the distillation (e) into the corresponding isocyanate and alcohol in a continuous cleaving means, g) purifying the crude isocyanate obtained from (f) in at least one distillation and recycling distillation residues to the cleavage (e) and/or converting them with alcohol into urethanes and supplying them to reaction unit (b), and h) converting the reaction discharge from (f), which comprises a high proportion of urethanes and useful compounds, into urethanes again, by reaction with alcohols.

The process of the invention features shorter residence times for attaining a specified conversion and hence features a better space-time yield than prior-art processes, especially the process known from EP 566 925.

In purely formal terms the process of the invention can be considered diagrammatically to be balanced by the following equation:

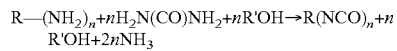

$$R\text{---}(NH_2)_n + nH_2N(CO)NH_2 + nR'OH \rightarrow R(NCO)_n + n R'OH + 2nNH_3$$

Amines suitable for preparing the monomeric polyurethanes which can be used as intermediates in accordance with the invention are amines of the formula $R(NH_2)_n$, in which R is a polyvalent, preferably divalent, organic radical, such as an aromatic or, preferably, a linear or branched-chain, aliphatic or cycloaliphatic radical which is un-substituted or substituted, for example, by an alkyl group.

Examples that may be mentioned of suitable aromatic polyamines include 2,4- and 2,6-tolylenediamine, 4,4'-, 2,4'-, and 2,2'-diaminodiphenylmethanes and the corresponding isomer mixtures.

Examples of suitable aliphatic or cycloaliphatic polyamines include the following: butane-1,4-diamine, 2-ethylbutane-1,4-diamine, octane-1,8-diamine, decane-1,10-diamine, dodecane-1,12-diamine, cyclohexane-1,4-diamine, 2-methyl- and 4-methyl-cyclohexane-1,3-diamine, and 1,3- and 1,4-diaminomethylcyclohexan. Preference is given to using 2-methylpentane-1,5-diamine, 2,2,4- and 2,4,4-trimethylhexane-1,6-diamine and, in particular, hexane-1,6-diamine and 3-aminomethyl-3,5,5-trimethylcyclohexylamine.

Suitable alcohols include in principle all aliphatic alcohols. However, preference is given to selecting those whose boiling points are sufficiently far removed from the boiling point of the polyisocyanate, preferably diisocyanate, obtained as a result of the thermal cleavage to allow quantitative or near-quantitative separation of the cleavage products—polyisocyanate, preferably diisocyanate and alcohol.

For these reasons, therefore, preference is given to using alcohols, such as methanol, ethanol, n-propanol, n-butanol, isobutanol, n-pentanol, isopentanol, n-hexanol, isohexanols, cyclohexanol, 2-ethylhexanol, decanol or mixtures of said alcohols, but especially n-butanol and/or isobutanol.

The individual stages of the process are described in the text below.

a) Mixing of the Reaction Components

To prepare the urethanes in reaction stage (a) the amines are reacted with urea and at least one, preferably exactly one, alcohol in a molar ratio of amine, urea, and alcohol of 1:2 to 20:5 to 40 at temperatures of 50-300° C. and in particular at 180-220° C. under a pressure of 0.1 to 30 bar, preferably 5-20 bar. These reaction conditions result in average reaction times for the process of the invention that range from fractions of seconds up to minutes.

The reaction in reaction stage (a) can be carried out in the presence of dialkyl carbonates, advantageously in an amount of 0.1 to 30 mol %, preferably 1 to 10 mol %, or of alkyl carbamates, advantageously in an amount of 1 to 20 mol %, preferably of 5 to 15 mol %, based on the polyamine, preferably diamine. Use is made in particular here of mixtures of dialkyl carbonates and alkyl carbamates in the stated proportions. Dialkyl carbonates and/or carbamic esters employed are preferably those whose alkyl radicals match the alkyl radical of the alcohol used.

As already stated, the reaction in reaction stage (a) can also take place in the presence of catalysts. They are used advantageously in amounts of 0.001% to 20% by weight, preferably 0.001% to 5% by weight, and in particular 0.01 to 0.1% by weight, based on the weight of the amine.

Catalysts suitable are organic or inorganic compounds comprising one or more cations, preferably a cation of metals from group IA, IB, IIA, IIB, IIIB, IVA, IVB, VA, VB, VIIB, VIIIB or VIIIB of the Periodic Table of the Elements, defined in accordance with Handbook of Chemistry and Physics 14th Edition, published by Chemical Rubber Publishing Co., 23 Superior Ave. N.E., Cleveland, Ohio, (US). Mention may be made by way of example of the cations of the following metals: lithium, sodium, potassium, magnesium, calcium, aluminum, gallium, tin, lead, bismuth, antimony, copper, silver, gold, zinc, mercury, cerium, titanium, vanadium, chromium, molybdenum, manganese, iron, and cobalt.

The catalyst may further comprise at least one anion, examples being halides, such as chlorides and bromides, sulfates, phosphates, nitrates, borates, alkoxides, phenoxides, sulfonates, oxides, oxide hydrates, hydroxides, carboxylates, chelates, carbonates, and thio- or dithiocarbamates.

The catalysts can also be employed, with no apparent marked disadvantages, in the form of their hydrates or ammoniates.

As typical catalysts mention may be made, by way of example, of the following compounds: lithium methoxide, lithium ethoxide, lithium propoxide, lithium butoxide, sodium methoxide, potassium tert-butoxide, magnesium methoxide, calcium methoxide, tin(II) chloride, tin(IV) chloride, lead acetate, lead phosphate, antimony(III) chloride, antimony(V) chloride, aluminum acetylacetonate, aluminum isobutoxide, aluminum trichloride, bismuth(III) chloride, copper(II) acetate, copper(II) sulfate, copper(II) nitrate, bis (triphenyl-phosphinoxido) copper(II) chloride, copper molybdenate, silver acetate, gold acetate, zinc oxide, zinc chloride, zinc acetate, zinc acetonylacetate, zinc octoate, zinc oxalate, zinc hexoxide, zinc benzoate, zink undecoxide, cerium(IV) oxide, uranyl acetate, titanium tetrabutoxide, titanium tetrachloride, titanium tetraphenoxide, titanium naphthenate, vanadium(III) chloride, vanadium acetylacetonate, chromium(III) chloride, molybdenum(VI)-oxide, molybdenum acetylacetonate, tungsten(VI) oxide, manganese(II) chloride, manganese(II) acetate, manganese(III) acetate, iron (II) acetate, iron(III) acetate, iron phosphate, iron oxalate, iron(II) chloride, iron(III) bromide, cobalt acetate, cobalt chloride, cobalt sulfate, cobalt naphthenate, nickel chloride, nickel acetate and nickel naphthenate, and mixtures thereof.

As preferred catalysts mention may be made, by way of example, of the following compounds: lithium butoxide, aluminum acetylacetonate, zinc acetylacetonate, titanium tetrabutoxide, and zirconium tetrabutoxide.

In the process of the invention the reactant streams are mixed in a suitable, special mixing means which is characterized by low mixing times.

The mixing time in said mixing means is usually from 0.0001 s to 2 s, preferably from 0.0005 to 1 s, more preferably from 0.001 to 0.5 s, very preferably from 0.005 to 0.2 s, and in particular from 0.007 to 0.1 s. The mixing time means the time which elapses from the beginning of the mixing operation until 97.5% of the fluid elements of the resultant mixture have a mixture fraction which, based on the theoretical final value of the mixture fraction of the resulting mixture when a state of perfect mixing has been reached, deviates by less than 2.5% from this final mixture-fraction value (regarding the concept of the mixture fraction see, for example, J. Warnatz, U. Maas, R. W. Dibble: Verbrennung, Springer Verlag, Berlin Heidelberg N.Y., 1997, 2nd edition, p. 134).

A preferred mixing means used is a mixing circuit, a stirred vessel, a mixing pump or a jet mixing means, such as coaxial mixing nozzles, Y- or T-mixer, or a vortex impinging-jet mixing configuration, preferably a mixing circuit, a stirred vessel, a mixing pump or a jet mixing means.

When using a mixing circuit or a stirred vessel as mixing means it is important to inject the amine solution at high speed. The speeds are normally between 10 and 100 m/s, preferably between 20 and 80 m/s.

It is preferred to use a mixing nozzle and a mixing pump as mixing means. It is particularly preferred to use, as mixing means, a mixing nozzle. In this case it is important that not only the alcohol reactant stream but also the amine reactant stream are introduced at high speed into the mixing nozzle. The speeds are between 10 and 100 m/s, preferably between 20 and 80 m/s.

The pressure in the feed lines to the nozzle is considerably higher than in the outlet of the mixing nozzle, but usually not higher than 110 bar abs, preferably not higher than 100 bar abs, the pressure being with particular preference from 5 to 95 bar abs, very preferably from 10 to 50 bar abs, and in particular from 10 to 30 bar abs.

The pressure at the outlet of the mixing means is generally above the reaction pressure in stage b): for example, it is between 5 and 100 bar, preferably between 10 and 80 bar, more preferably between 10 and 50 bar.

The temperature of the discharge from the mixing means is generally between 25 and 240° C., preferably 30-190° C., and more preferably 40-180° C.

Before being introduced into stage b), the discharge from the mixing means can be brought by means of a heat exchanger to the temperature desired therein.

The conversion, based on amino groups in the amine employed to urethane groups, in stage a) is generally not more than 10%, preferably not more than 5%, more preferably not more than 2%.

The transfer of the reaction discharge from stage a) to the subsequent stage can take place advantageously via pressure maintenance valves, it being intended that the pressure at the exit from stage a) should be at least 1 bar, preferably at least 2 bar, more preferably at least 3 bar above the pressure prevailing in stage b).

b) Reaction of the Mixture from a)

The liquid phase leaving the mixing means is then supplied to at least one, preferably precisely one, tube reactor which is operated with two phases (gaseous/liquid), or to two or more reactors which from their residence-time distribution resemble a tube reactor, and in which the gas phase is guided with the liquid phase in cocurrent flow.

The tube reactor ought preferably to be very largely free from backmixing. This is achieved, for example, by means of the ratio of the diameter of the tube reactor to its length or by means of internals, such as perforated plates, slotted plates or static mixers. The freedom from backmixing is preferably achieved through the ratio of length to diameter of the tube reactor.

Suitable tube reactors include for example tubes whose length-to-diameter ratio is greater than 5, preferably greater than 6, more preferably greater than 10.

The Bodenstein number of the tube reactor ought to be greater than 5, preferably greater than 6, more preferably greater than 10, very preferably from 10 to 600, and in particular from 10 to 100.

One aspect making a substantial contribution to the invention is the existence of flow which ideally is a plug flow (piston flow) and in reality is to be approximated to such a flow as far as is necessary. For that purpose the axial mixing, i.e., mixing along the flow direction through the reactor, is reduced as much as possible, and ideally the flow is turbulent.

This is achieved in practice by means of high flow rates and low cross-sectional areas in, for example, flow tubes.

The tube reactor may have any desired orientation in space. It is preferably constructed as a vertical tube reactor which with particular preference is flow-traversed from bottom to top.

The tube reactor may be of isothermal or, preferably, temperature-conditioned configuration. Temperature conditioning can be accomplished by means of jacket heating or by means of internal tubes or plates. Heating takes place preferably through the jacket.

The tube reactor may of course also be composed of two or more serial tube sections, provided the freedom from backmixing is still ensured. If necessary it is possible optionally to provide phase separators for separating liquid from gaseous phase along the course of the tube reactor—for example, between tube sections of the aforementioned kind—in which ammonia formed during the reaction can be separated off, so that the equilibrium of the reaction is shifted.

To increase the production capacity it is also possible in accordance with the invention to connect two or more tube reactors in parallel.

If appropriate it is possible, as remarked above, to meter in further urea and/or alcohol or, preferably, amine at one or more points—for example, at the beginning and in the middle of the tube reactor.

The average residence time in the tube reactor is generally 10 seconds to 5 hours, preferably 20 seconds to 20 minutes, and more preferably 30 seconds to 10 minutes.

In order to keep the gas loading on the subsequent stage low it is possible to supply the discharge from the tube reactor, in one preferred embodiment, to a phase separator, and the liquid phase taken from the phase separator can then be supplied to the subsequent stage.

A phase separator of this kind is a vessel in which phase separation between gas phase and liquid phase is achieved through the calming of the two-phase flow emerging from the cocurrent reactor.

The phase separator may be of isothermal or, preferably, heated configuration, in order to prevent precipitation of low-solubility by products. Heating may take place, for example, via the jacket or via a circuit with an external heat exchanger. When an external heat exchanger is used, standard insulation of the heat exchanger is sufficient.

The temperature in the tube reactor and in any phase separator present is generally between 50° C. and 300° C., preferably between 180° C. and 220° C.

The pressure in stage b) is generally between 0.1 bar abs and 30 bar abs, and preferably between 5 and 20 bar abs.

The transfer of the reaction discharge from stage b) into the subsequent stage can take place advantageously via pressure maintenance values, the intention being that the pressure in stage b) ought in general to be at least 0.1 bar above the pressure prevailing in stage c). If this is not the case, transfer may take place with the aid, for example, of a pump, or barometrically.

The residence time in stage b) is selected such that the conversion, based on amino groups in the amine employed to urethane groups, following departure from the tube reactor is at least 95%, preferably at least 98%, more preferably at least 99%, and very preferably at least 99.5%.

The total residence time in stages a) and b) together is usually less than 5 hours, preferably less than 4 hours, and more preferably less than 3 hours.

In the case of complete conversion of the amines to the urethane, the discharge of the reaction mixture from b) can be supplied directly to the ammonia separation stage c), or else the reaction mixture discharge is supplied to a further reactor or reactor system for attainment of complete conversion. Reactors employed by may be further tube reactors, mixing-reactor cascades or columns exhibiting the necessary average residence time.

If the conversion, based on amino groups in the amine used to urethane groups, following departure from the tube reactor is still not complete, and if for example it is less than 95%, the discharge can be further reacted again.

For that purpose the reaction mixture, in order to complete the conversion, can be after reacted in a further tube reactor or else in a backmixed reactor, preferably until the conversion amounts to 98% or more.

A backmixed reactor system here is one whose Bodenstein number is less than 5, preferably less than 4.

c) Ammonia Separation

To separate off the ammonia it is advantageous to use columns; the ammonia is preferably separated off by distillation. This produces effective separation between the alcohol and ammonia. Normally the separation takes place in a pressure range of 0.01-20 bar, preferably at 0.04-15 bar. The requisite temperatures are guided by alcohol or alcohol mixture used. For n-butanol the temperature, for example, is 60-150° C., preferably 80 to 140° C.

It has proven advantageous to separate off the ammonia form from the reaction mixture immediately, thereby making it possible to prevent coating with ammonium carbamate, which is formed in minimal amounts from ammonia and the carbon dioxide as a result of urea decomposition.

This distillation unit is of conventional construction and has the usual internals. Suitable column internals include in principle all customary internals, examples being trays, structured packings and/or random packings. Preference among the trays is given to bubble-cap trays, sieve trays, valve trays, Thorman trays and/or dual-flow trays, and, among the random packings, to those featuring rings, coils, saddles, Raschig, Intos or Pall rings, Barrel or Intalox saddles, Top-Pak, etc., or meshes. It is preferred to use trays, more preferably bubble-cap trays.

The distillation column preferably has 10-20 theoretical plates.

d) Separation of the Excess Alcohol

Subsequently alcohol, dialkyl carbonates, if formed or present in the reaction mixture, or alkyl carbamates, or mixtures of at least two of these components, are separated off from the ammonia-depleted reaction mixture obtained and are recycled preferably to reaction stage (a) and/or (b).

To separate off the components the reaction mixture is depressurized advantageously from the pressure level of reaction stage (b) to a pressure in the range from 1 to 500 mbar, preferably from 10 to 100 mbar. This produces gaseous vapors which comprise the predominant amount of alcohol along with 0 to 30%, preferably 1% to 10%, by weight of dialkyl carbonate and/or 1 to 50%, preferably 1% to 20%, by weight of alkyl carbamate, and a liquid discharge which is composed essentially of the monomeric polyurethane, preferably diurethane, and which if appropriate comprises oligourea-polyurethanes and high-boiling oligomers.

The vapors obtained ($d_L$) are separated in downstream purification stages which advantageously work by distillation, preferably by rectification, and the useful products isolated in these purification stages, namely alcohol and alkyl carbamate, individually or as a mixture, are recycled preferably to reaction stage (a) for the formation of the monomeric polyurethanes.

For the distillative separation of the alcohol or alcohol mixture, use is frequently made of what is called a flash. This apparatus may be a vessel or a combination of vessel and column, preferably a column, with the alcohol or alcohol mixture able to be taken off at the top and the urethane in the liquid phase. At the top of the column there may be not only the alcohol but also further compounds which boil more readily than the urethane. Separation takes place within a pressure range of 0.001 to 1 bar, preferably at 0.02-0.5 bar.

e) Urethane Purification

The liquid reaction mixture (d) obtained in reaction stage (d), after the vapors have been separated off, generally in the form of a liquid-phase discharge, and comprising the monomeric polyurethanes, preferably diurethanes, and, if appropriate, oligourea-polyurethanes and high-boiling oligomers, either can be passed completely to the sub-sequent stage or, preferably, is divided into two substreams, the weight ratio of the portions being 5 to 50:95 to 50 parts by weight, preferably 10 to 30:90 to 70 parts by weight.

The equal-sized or, preferably, smaller portion is separated distillatively by means of a conventional distillation unit, preferably a thin-film evaporator, at a temperature of 170 to 240° C., preferably of 180 to 230° C., and under a pressure of 0.001-1 bar, preferably 0.002-0.01 bar, into a useful product which comprises the polyurethanes, preferably diurethanes, and the relatively readily boiling byproducts ($e_L$), and undistillable byproducts ($e_H$), which are separated off from the preparation process and usually discarded as an unusable residue. The useful product (distillate) is combined with the equal-sized or, preferably, larger, other portion, and the combined reaction mixture, comprising polyurethanes, preferably diurethanes is supplied to the thermal cleavage operation (f).

As a result of this process measure in reaction stage (e) the fraction of undistillable by products in the reaction mixture, which form during the sequential component reactions and which would accumulate continuously as a result of the recycling of useful feedstock in the reaction circulation, is limited to an amount of 3% to 30% by weight, preferably 5% to 20% by weight, and hence a reaction which proceeds with high selectivity and without disruption is ensured.

Distillation equipment employed may comprise thin-film evaporators or short-path evaporators. The urethane is distilled at pressures of 0.001-1 bar, preferably in the range of 0.002-0.01 bar. The distillate ($e_L$) is supplied to the cleavage operation (f).

The bottom product ($e_S$), containing high boilers, is preferably discarded or, less preferably, can be supplied in part to the reurethanization (h).

f) Urethane Cleavage

The reaction mixture obtained in reaction stage (e) and comprising polyurethanes, preferably diurethanes, is subjected to continuous thermal cleavage in a suitable apparatus, preferably solventlessly in liquid phase, in the presence of catalysts, at temperatures of 200 to 300° C., preferably 220 to 280° C., and under reduced pressure of 0.01-0.6 bar, preferably in the range of 0.02-0.1 bar. The conversion of polyurethane to polyisocyanate, preferably of diurethane to diisocyanate, in the thermal cleavage apparatus can be selected largely freely as a function of the polyurethane used, and is situated advantageously in a range from 10% to 98% by weight, preferably 40% to 90% by weight of the amount of polyurethane supplied.

The uncleaved fraction of the reaction mixture, comprising unreacted polyurethanes, oligourea-polyurethanes, high-boiling oligomers, and other reusable or unusable byproducts, is separated off, diverted continuously from the cleavage apparatus (1H) and recycled directly or, if appropriate, after reaction with alcohol in the reurethanization (h) to reaction stage (a) and/or (b).

Examples of catalysts used for the chemical cleavage of the polyurethanes include the aforementioned organic and inorganic compounds that catalyze urethane formation.

Catalysts which have proven particularly appropriate and are therefore used with preference include dibutyl tin dilaurate, iron(III) acetylacetonate, cobalt(II) acetylacetonate, zinc acetylacetonate, zirconium tetra-n-butoxide, and tin(II) dioctoate.

Examples of suitable cleavage apparatus include cylindrical cleavage reactors, such as tube ovens or, preferably, evaporators, examples being thin-film or bulk evaporators, such as Robert evaporators, Herbert evaporators, caddle-type evaporators, plate-type cleavers, and, preferably, heating-cartridge evaporators.

The cleavage products are separated in a column in which, customarily, the isocyanate is taken off at the side ($f_M$) and the alcohol ($f_L$) at the top.

g) Isocyanate Purification

The crude isocyanate mixture is freed in a downstream distillation from recombination products, by products, and, where present, the solvent. The by products are preferably recycled to the thermal cleavage. A portion may also be diverted out.

The cleavage products formed during the thermal cleavage, composed primarily of alcohol, polyisocyanate, preferably diisocyanate, and partly cleaved polyurethanes, are subsequently separated by means, advantageously, of one or more distillation columns, preferably by rectification at temperatures of 100 to 220° C., preferably 120 to 170° C., under a pressure of 1 to 200 mbar, preferably 5 to 50 mbar, into low boilers, and particularly alcohol ($g_L$), and a crude polyisocyanate mixture ($g_M$) having a polyisocyanate content of 85% to 99% by weight, preferably of 95% to 99% by weight. The higher-boiling by products ($g_H$) obtained in the course of the distillative separation, and especially the uncleaved and partly cleaved polyurethanes, are guided preferably into the cleavage apparatus (f) and/or reurethanization (h).

The index "L" here identifies low-boiling streams of the individual stages, the index "H" high-boiling streams, and "M" middle-boiling streams.

The crude polyisocyanate mixture ($g_M$) obtained preferably by rectification is purified by distillation at a temperature of 100 to 180° C. under a pressure of 1 to 50 mbar, the individual fractions being recycled or isolated as a pure product. As has already been observed, the top fraction in the purifying distillation that is preferably employed, said fraction being composed preferably of polyisocyanate, especially diisocyanate, is recycled to reaction stage (a) and/or (b), the free isocyanate groups having if appropriate been reacted with alcohol; the side fraction, which is composed of pure polyisocyanate, especially diisocyanate, preferably having a purity of at least 98% by weight, in particular more than 99% by weight, is led off and passed on for storage; and the bottom fraction, whose essential components are the partly cleaved polyurethanes and polyisocyanates, is preferably recycled to the cleavage apparatus (f) for thermal cleavage.

According to other versions of the process, alternatively, the bottom fraction ($g_H$) can be recycled to the distillation column (d) for separation from crude polyisocyanate and alcohol, or to reaction stage (a) and/or (b), the formation of polyurethane. It is also possible to divide the bottom fraction into two or three product streams, which are recycled preferably to the polyurethane formation stage (a) and to the cleavage apparatus (f), and also, if appropriate, to the distillation column (g) or to the reurethanization (h).

h) The reaction of the reaction discharge ($f_H$) from f) and/or distillation residues ($g_H$) from (g) are preferably supplied again to the process. Using alcohol, the isocyanate groups comprised in this mixture, and/or allophanates and/or ureas or other reactive constituents, are converted into urethanes. The possibility exists of carrying out these reactions in separate reactors, such as mixing reactors or flow tubes, or else in (b).

Alcoholysis of the residues requires temperatures of 100-250° C., preferably 150-220° C. The average residence times in this case are situated in the range from a few minutes up to hours.

For this purpose it is possible, for example, to combine the flows ($f_H$) and/or ($g_H$) and also, if appropriate, part of the flow ($e_H$) with alcohol, the molar ratio of NCO groups and/or equivalents thereof, i.e., urethane groups for example, to hydroxyl groups being up to 1:100, preferably up to 1:20, more preferably up to 1:10.

The alcohol here may be, for example, the low-boiling stream ($d_L$) from stage (d) and/or the alcohol-containing stream ($f_L$) from the urethane cleavage (f) and/or else fresh alcohol.

The reaction mixture is reacted in the presence or absence of catalysts within a period of 1 to 150 minutes, preferably 3 to 60 minutes, at a temperature of 20 to 200° C., preferably 50 to 170° C., under a pressure of 0.5 to 20 bar, preferably 1 to 15 bar.

The reaction can be carried out in a continuous tank cascade or in a tube reactor. Suitable catalysts include in principle all compounds which promote the reaction of NCO groups with OH groups. Examples that may be mentioned include tin octoate, dibutyltin dilaurate, tin chloride, zinc dichloride, tin(II) dioctoate, and triethylamine.

With the multistage process of the invention for continuously preparing organic polyisocyanates, with recycling and removal of the by products, it is possible to prepare distillable polyisocyanates, preferably diisocyanate, with high selectivity and in very good yields.

The process of the invention is especially suitable for preparing aliphatic diisocyanates, such as 2-methylpentane 1,5-diisocyanate, isomeric aliphatic diisocyanates having 6 carbon atoms in the alkylene radical, and mixtures thereof, and, preferably, hexamethylene 1,6-diisocyanate, and cycloaliphatic diisocyanates, especially 3-isocyanatomethyl-3,5,5-trimethylcyclohexyl isocyanate, in accordance with an economical method.

The polyisocyanates prepared are suitable preferentially for producing plastics comprising urethane, isocyanurate, amide and/or urea groups by the polyisocyanate polyaddition process. They find use, furthermore, for the preparation of polyisocyanate mixtures modified with urethane, biuret and/or isocyanurate groups. Polyisocyanate mixtures of this kind, comprising aliphatic or cycloaliphatic diisocyanates, are used particularly for producing light-stable polyurethane paints and coatings.

According to one preferred embodiment the top fraction obtained in the distillative purification of the crude polyisocyanate (f) is recycled to reaction stage (a); the side fraction, which is composed of substantially pure polyisocyanate, is passed to a container for storage; and the bottom fraction is recycled to reaction stage (a) or (d) or else to (a) and (d).

The examples which follow are intended to illustrate the invention but not to restrict it to these examples.

INVENTIVE EXAMPLE

A vessel (A) was charged with 1,6-hexamethylenediamine at a temperature of 80° C. A second vessel was charged with butanol (B). A reaction mixer (reaction mixer HMR from K-Engineering, reaction volume 5 ml, 4000 min$^{-1}$) was supplied by means of pumps with a flow of 0.9 kg/h amine, 8 kg/h butanol, and 1.8 kg/h liquid urea (C). Using heat transfer means, the flows were preheated so that the temperature in the nozzle (D) was at least 130° C. to 150° C.

The reaction mixture then flowed through a jacket-heated tube reactor (E) having a length of 6 m (Bodenstein number: approximately 40), an average residence time of a few seconds, and a Reynolds number of approximately 10000.

The reaction mixture from the flow tube is subsequently left to reside in a mixing reactor (F) until conversion of the amine is complete, with an average residence time of approximately 4 hours. The temperature in the reactor, at a pressure of 11 bar, is approximately 215° C. The reaction discharge comprises approximately 2.4 kg/h hexamethylenedibutylurethane and can, as is known, be cleaved to form 1,6-hexamethylene diisocyanate and worked up.

COMPARATIVE EXAMPLE

The first reactor in a three-stage tank cascade is charged with 0.8 kg/h 1,6-hexamethylenediamine, 0.88 kg/h urea and 1.1 kg/h n-butanol. All of the reactors are operated under a pressure of approximately 11.5 bar. The temperatures are situated in the range of 215-230° C. The ammonia formed during the reaction is separated off by means of columns and a butanol condensation facility. The average residence time of the liquid in the tank cascade is approximately 5 hours. The thermal energy needed for the reaction and evaporation is introduced through the reactor jacket. From the final reactor there departs a reaction mixture comprising approximately 2.1 kg/h dibutylurethane.

The inventive example shows that achieving the same conversion in a reactor configuration in accordance with the present invention requires a shorter residence time than with a reactor configuration of a kind known from the prior art.

The invention claimed is:

1. A process comprising preparing isocyanates by reacting at least one amine with urea and at least one alcohol to the corresponding urethane in at least one mixer, thereby forming a reaction mixture, and then flowing the reaction mixture to at least one residence-time reactor attached to said mixer and subsequently cleaving the resultant urethane into the corresponding isocyanates,
   wherein conversion, based on amino groups in the amine employed to urethane groups, is not more than 10% in said mixer,
   wherein the pressure at the outlet of the mixer is between 5 and 100 bar and is above the reaction pressure in the residence-time reactor(s) by at least 1 bar.

2. The process according to claim 1, wherein said mixer is selected from the group consisting of mixing circuit, mixing pump, jet mixer, coaxial mixing nozzles, Y-mixer, T-mixer, and vortex impinging-jet mixing configuration.

3. The process according to claim 1, wherein the mixing time in the mixer is from 0.0001 to 2 s.

4. The process according to claim 1, wherein alcohol and amine are introduced into the, mixer at a speed between 10 and 100 m/s.

5. The process according to claim 1, wherein the residence-time reactor is a tube reactor.

6. The process according to claim 5, wherein the tube reactor has a Bodenstein number of more than 5.

7. The process according to claim 1, wherein the amine is a diamine.

8. The process according to claim 1, wherein the amine is selected from the group consisting of butane-1,4-diamine, 2-ethylbutane-1,4-diamine, octane-1,8-diamine, decane-1,10-diamine, dodecane-1,12-diamine, cyclohexane-1,4-diamine, 2-methyl-, and 4-methyl-cyclohexane-1,3-diamine, 1,3- and 1,4-diaminomethylcyclohexane, 2-methylpentane-1,5-diamine, 2,2,4- and 2,4,4-trimethylhexane-1,6-diamine, hexane-1,6-diamine, and 3-aminomethyl-3,5,5-trimethylcyclohexylamine.

9. The process according to claim 1, wherein the alcohol is selected from the group consisting of methanol, ethanol, n-propanol, n-butanol, isobutanol, n-pentanol, isopentanol, n-hexanol, isohexanols, cyclohexanol, 2-ethylhexanol, decanol, and mixtures of said alcohols.

10. A method for reacting at least one amine with urea and at least one alcohol to form the corresponding urethane which comprises use of a mixer selected from the group consisting of a mixing circuit, mixing pump, jet mixer, coaxial mixing nozzles, Y-mixer, T-mixer and vortex impinging-jet mixing configuration.

11. The process according to claim 1, wherein the mixing time in the mixer is from 0.0005 to 1 s.

12. The process according to claim 1, wherein the mixing time in the mixer is from 0.007 to 0.1 s.

13. The process according to claim 1, wherein conversion, based on amino groups in the amine employed to urethane groups, is at least 95% after departure from said residence-time reactor.

14. The process according to claim 1, wherein conversion, based on amino groups in the amine employed to urethane groups, is not more than 2% in said mixer and at least 99.5% after departure from said residence-time reactor.

15. The process according to claim 5, wherein the tube reactor has a Bodenstein number of from 10 to 100.

16. The process according to claim 5, wherein the average residence time in the tube reactor is from 10 seconds to 5 hours.

17. The process according to claim 5, wherein the average residence time in the tube reactor is from 30 seconds to 10 minutes.

18. The process according to claim 5, wherein the total residence time in the mixer and the tube reactor is less than 5 hours.

19. The process according to claim 5, wherein the total residence time in the mixer and the tube reactor is less than 4 hours.

20. The process according to claim 5, wherein the total residence time in the and the tube reactor is less than 3 hours.

21. The process according to claim 1, wherein said mixer is selected from the group consisting of a mixing pump and a mixing nozzle.

* * * * *